United States Patent
Egorov et al.

(10) Patent No.: US 8,052,622 B2
(45) Date of Patent: Nov. 8, 2011

(54) METHODS FOR CHARACTERIZING VAGINAL TISSUE ELASTICITY

(75) Inventors: Vladimir Egorov, Princeton, NJ (US); Armen P. Sarvazyan, Lambertville, NJ (US)

(73) Assignee: Artann Laboratories Inc, Trenton, NJ (US)

( * ) Notice: Subject to any disclaimer, the term of this patent is extended or adjusted under 35 U.S.C. 154(b) by 0 days.

(21) Appl. No.: 12/874,583

(22) Filed: Sep. 2, 2010

(65) Prior Publication Data

US 2011/0054357 A1     Mar. 3, 2011

Related U.S. Application Data

(60) Provisional application No. 61/239,087, filed on Sep. 2, 2009.

(51) Int. Cl.
*A61B 5/117* (2006.01)
*A61B 5/103* (2006.01)

(52) U.S. Cl. ........................................ 600/591

(58) Field of Classification Search ............... 600/587, 600/462, 591; 707/1
See application file for complete search history.

(56) References Cited

U.S. PATENT DOCUMENTS

| | | | |
|---|---|---|---|
| 4,947,851 A | 8/1990 | Sarvazyan | |
| 5,115,808 A | 5/1992 | Popovic | |
| 5,265,612 A | 11/1993 | Sarvazyan | |
| 5,524,636 A | 6/1996 | Sarvazyan | |
| 5,678,565 A | 10/1997 | Sarvazyan | |
| 5,706,815 A | 1/1998 | Sarvazyan | |
| 5,785,663 A | 7/1998 | Sarvazyan | |
| 5,810,731 A | 9/1998 | Sarvazyan | |
| 5,833,633 A | 11/1998 | Sarvazyan | |
| 5,836,894 A | 11/1998 | Sarvazyan | |
| 5,860,934 A | 1/1999 | Sarvazyan | |
| 5,922,018 A | 7/1999 | Sarvazyan | |
| 6,091,981 A | 7/2000 | Cundari | |
| 6,142,959 A | 11/2000 | Sarvazyan | |
| 6,468,231 B2 | 10/2002 | Sarvazyan | |
| 6,569,108 B2 | 5/2003 | Sarvazyan | |
| 6,595,933 B2 | 7/2003 | Sarvazyan | |
| 6,620,115 B2 | 9/2003 | Sarvazyan | |
| 2004/0117343 A1* | 6/2004 | Johnson | 707/1 |
| 2007/0167819 A1* | 7/2007 | Osborn et al. | 600/462 |
| 2008/0077053 A1* | 3/2008 | Epstein et al. | 600/591 |
| 2010/0087756 A1* | 4/2010 | Egorov et al. | 600/587 |

OTHER PUBLICATIONS

Egorov V, Van Raalte H, Sarvazyan AP. Vaginal tactile imaging. IEEE Trans Biomed Eng. Jul. 2010; 57 (7):1736-44. Epub May 17, 2010.

* cited by examiner

*Primary Examiner* — Brian Szmal
(74) *Attorney, Agent, or Firm* — Boris Leschinsky

(57) ABSTRACT

Methods for characterizing elasticity of vaginal tissue are provided. A transvaginal probe is used to deform vaginal tissue during examination. The probe is equipped with pressure sensors and a motion tracking sensor. Stress and strain data is recorded during examination. Elasticity of vaginal tissue is then characterized by calculating a stress gradient defined as a ratio of stress over strain for each point of measurement. Vaginal tactile image may also be compiled to include a family of surfaces representing locations of measurement points at predefined constant levels of stress. Pelvic organ abnormality condition may be detected if the stress gradient is below either a predetermined threshold or a normal stress gradient obtained from clinical data.

12 Claims, 4 Drawing Sheets

METHODS FOR CHARACTERIZING VAGINAL TISSUE ELASTICITY

CROSS-REFERENCE DATA

This application claims a priority date benefit from the U.S. Provisional Application No. 61/239,087 filed 2 Sep. 2009 entitled "METHODS OF USING A VAGINAL TACTILE IMAGER FOR PELVIC ORGAN PROLAPSE CHARACTERIZATION, INCLUDING THAT AFTER A RECONSTRUCTIVE SURGERY", which is incorporated herein by reference in its entirety.

REFERENCE TO GOVERNMENT-SPONSORED RESEARCH

This invention was made with the U.S. government support under SBIR grant No. AG034714 entitled "Vaginal Tactile Imager for Pelvic Floor Biomechanical Assessment" and awarded by the National Institute of Health, National Institute on Aging. The government has certain rights in this invention.

BACKGROUND OF THE INVENTION

The present invention generally relates to objective characterization methods for female pelvic tissues. Specifically, the invention describes methods for characterizing vaginal tissue elasticity and detection of a pelvic organ abnormality. For the purposes of this description, the terms "pelvic organ abnormality", "pelvic floor abnormality" and "vaginal abnormality" are used interchangeably.

Various stages of pelvic organ abnormality including a pelvic organ prolapse (POP) are highly prevalent affecting at least 50% of women in the US during their lifetimes. Some loss of utero-vaginal support occurs in most adult women. POP is the extreme case of descent of the apex of the vagina or cervix (or vaginal vault after hysterectomy), anterior vaginal wall, and/or posterior vaginal wall. As abnormality progresses, pelvic organs can become displaced and even protrude outside the vaginal canal. POP is the leading indication for hysterectomy in postmenopausal women and accounts for 15-18% of procedures in all age-groups [Kesharvarz H, Hillis S D, Kieke B A, Marchbanks P A. Hysterectomy surveillance—United States 1994-1999. MMWR *Surveill Summ* 2002; 51 (5505):1-8]. Beyond the physical impact of POP, women with progressing pelvic organ abnormality score poorer on both generic and condition specific quality-of-life scales [Jelovsek J E, Barber M D. Women seeking treatment for advanced pelvic organ abnormality have decreased body image and quality of life. *Am J Obstet Gynecol*. 2006; 194: 1455-61.]. In addition, about one third of sexually active women with POP report that their condition interferes with sexual function [Barber M D, Visco A G, Wyman, et al. Sexual function in women with urinary incontinence and pelvic organ abnormality. *Obstet Gynecol*. 2002; 99:281-9.].

Clinical diagnosis of vaginal abnormalities and ultimately POP involves taking a medical history and performing a manual physical examination when a physician inspects the urogenital areas and rectum for masses and indication of reduced muscle tone. The physician instructs the patient to cough, bear down or perform a Valsalva maneuver (a forceful attempt at exhalation with the mouth and nose closed) to see if and how far the vagina descends as the result of the additional abdominal pressure [Shagam J Y. Pelvic organ prolapse. *Radiol Technol*. 2006; 77(5):389-400].

While physical examination helps the clinician describe the extent of pelvic floor prolapse, it does not help in discerning the initial stage of abnormality development from the normal condition. Digital palpation does not provide quantitative tissue characterization to compare with normal elasticity of vaginal walls. It has poor sensitivity and is highly subjective.

Changes in the elasticity of the vaginal walls, connective support tissues, and muscles are significant factors in the development of POP. The high incidence of POP dictates the need for new effective methods of objective vaginal tissue characterization and early abnormality detection.

SUMMARY OF THE INVENTION

The object of the present invention is to overcome the drawbacks of the prior art and to provide methods for objective characterizing of vaginal tissue elasticity, in particular using a transvaginal probe equipped with instruments to record tissue strain and stress data.

Another object of the invention is to provide methods for objective detection of pelvic organ abnormality.

A further object of the invention is to provide a method for detecting pelvic organ abnormality condition by comparing a calculated elasticity measure against a predetermined threshold.

A further yet object of the invention is to provide a method for objective detection of pelvic organ abnormality condition by comparing a calculated elasticity measure against a normal elasticity value obtained from clinical data collected from a number of patients.

In embodiments, the method for characterizing vaginal tissue elasticity includes the steps of deforming a vaginal tissue using a transvaginal probe; obtaining stress and strain data for one or more measurement points of the vaginal tissue; and calculating at least one stress gradient for the vaginal tissue so as to allow objective characterization of its elasticity.

The transvaginal probe of the invention includes pressure sensors and a motion tracking sensor, which allows recording both stress and strain data for one or more points of the vaginal tissue.

In embodiments, stress and strain data recorded for a plurality of measurement points is used to calculate average stress gradient for a preselected area of vagina. The value of the stress gradient may be then compared with a predefined numerical threshold such as for example 3 kPa/cm or with a normal stress gradient obtained from clinical data collected for other patients with known normal or diseased status for the vaginal tissue. Such comparison allows detecting of a pelvic floor abnormality condition is the calculated stress gradient falls below a threshold or a normal value.

In embodiments, the step of characterizing vaginal tissue elasticity may include composing a vaginal tactile image. One particularly useful way to graphically represent collected stress and strain data is to compile a family of surfaces together forming the vaginal tactile image. Each surface is drawn through locations of the measurement points when deformed at a particular constant level of stress. Selecting a number of different constant stress values defines a number of surfaces for the vaginal tactile image. Each constant stress location of the measurement point may be either an actually recorded location for a particular stress or a calculated location representing an extrapolation from other known locations and stresses assuming a linear model of tissue compression.

BRIEF DESCRIPTION OF DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF PREFERRED EMBODIMENTS OF THE INVENTION

Figure 1:
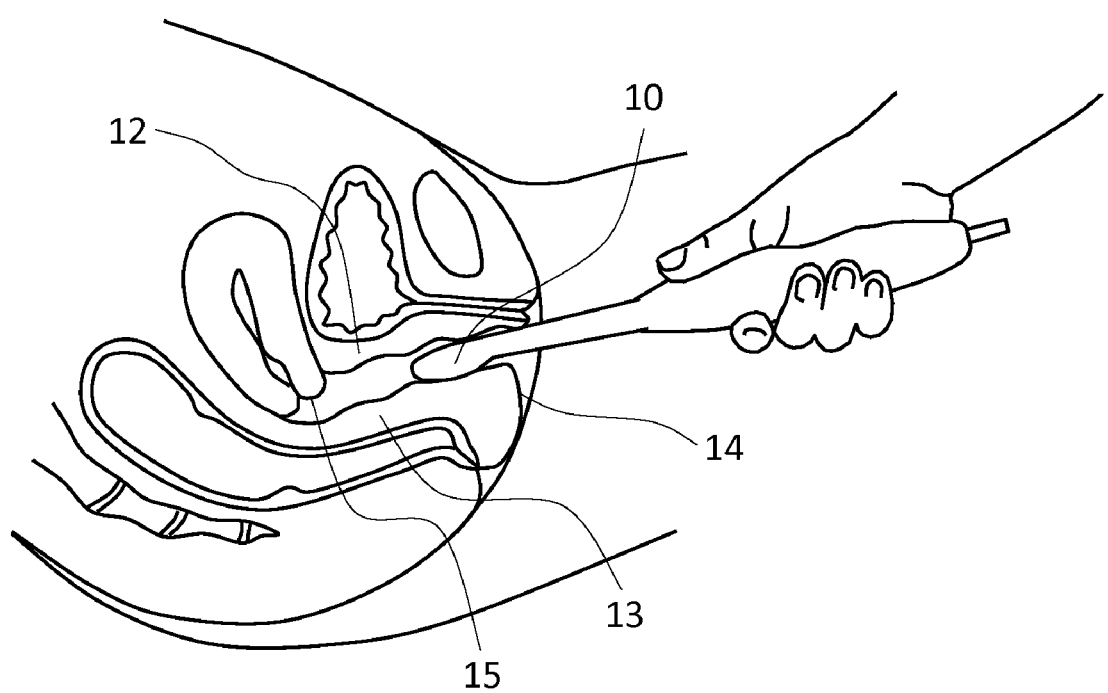
FIG. 1 illustrates vagina examination procedure using a transvaginal probe.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

FIG. 1 illustrates the examination procedure of the invention, which includes inserting a transvaginal probe 10 into a vagina. The probe is equipped with pressure sensors and a motion tracking sensor allowing acquisition of pressures and coordinates for each pressure sensor during vaginal tissue deformation. The examination includes deforming vaginal tissue for example by pressing or sliding the transvaginal probe 10 about at least one measurement point. In embodiments, deforming the tissue is conducted along a plurality of measurement points on either an anterior vaginal wall 12 and/or a posterior vaginal wall 13 from hymen 14 to cervix 15 while using the probe to apply pressure to vaginal walls. Obtained stress and strain data for the measurement points during deformation of vaginal tissue are used for calculating a stress gradient to characterize vaginal tissue elasticity. In embodiments, the stress and strain data is used to compose a vaginal tactile image. For sliding examinations, the range of pressures on the vaginal wall may be selected from about 1 kPa to about 10 kPa. For a compression mode of examination, the range of pressures may be selected to be from about 1 kPa to about 20 kPa. The examination procedure may further include repeating the vaginal tissue deformation resulting from pressing or sliding motion at least two and preferably up to five times while increasing the pressure applied by the transvaginal probe 10 in the predefined range. The examination procedure may further include real-time review of obtained stress and strain data and/or composed vaginal tactile image to provide guidance for an examiner. If an irregularity is discovered, the transvaginal probe 10 may be moved to the location of such irregularity and tissue deformation may be repeated. Full examination of the vagina may take as little as 3-5 minutes. Obtained data is stored in a digital format allowing a post-procedural review of collected data and composed vaginal tactile image.

A vaginal tactile imager includes a transvaginal probe 10 connected with an electronic unit (not shown) and further connected to a monitor such as a laptop computer with a data acquisition card. One particularly useful design incorporates a pressure sensor array that may be assembled on the distal part of the transvaginal probe 10 in the form of a one-dimensional or a two-dimensional pressure sensor array. This pressure sensor array may be placed along the surface of the transvaginal probe 10 configured for contacting the vaginal wall. In one embodiment, the transvaginal probe surface may have a convex form. The probe head may measure 50 mm in length, 20 mm in width, and 13 mm in height having an ellipsoidal cross-section. The pressure sensor array may for example comprise 120 (15×8) pressure sensors with dimensions of 2.5 mm by 2.5 mm, the entire array of sensors forming the total sensing area of about 40 mm by 20 mm. During examination, the transvaginal vaginal probe 10 may be covered by a thin disposable sheath configured not to affect the stress and strain measurements.

The motion tracking sensor of the transvaginal probe 10 is preferably a six degrees of freedom sensor allowing obtaining data on three angles and three coordinates, although a sensor with only three degrees of freedom (three angles or three coordinates) may also be used. The tracking sensor provides coordinates of all pressure sensors during the vaginal tissue deformation. In one embodiment, the sensor may provide motion tracking data in a coordinate system related to the pelvic floor skeleton.

The electronic unit includes a pressure sensor electronics adapted to communicate with a computer through a communication port. The data acquisition rate may be in the range from 15 up to 30 pressure frames per second.

The software of the transvaginal probe 10 supports at least three operational modes: data acquisition mode, data management mode, and device management mode. The software allows for real-time visualization of the pressure pattern on the probe head, composed vaginal tactile image and for storing the data in a digital format.

Deformations of the vaginal wall using different levels of applied pressure results in collecting stress and strain data for the vaginal tissue. Knowing the size of the vaginal probe and its movement inside the vagina allows the system of the invention to relate recorded contact pressure or stress values at each measurement point of the vaginal tissue (as obtained by a pressure sensor) to the geometrical coordinate of that measurement point as it is being displaced by the probe (using the motion tracking data). Therefore, examination the vagina with the transvaginal probe 10 results in a data set of applied pressures and corresponding spatial dislodgements of one or more measurement points for a vaginal tissue. At the end of the vaginal examination, each measurement point may be associated with a particular geometric motion trajectory. Stress data is recorded for at least two or preferably more locations of the measurement point along this trajectory.

Knowing measured stress data and associated geometrical locations for each measurement point allows calculating locations for each measurement point along their respective deformation trajectories for a given value of stress. Such locations may be calculated by extrapolating stress and strain data from measured values using for example a linear model of tissue compression. In embodiments, other more sophisticated models of tissue compression may also be used in place of a simple linear tissue deformation model.

Figure 2A:
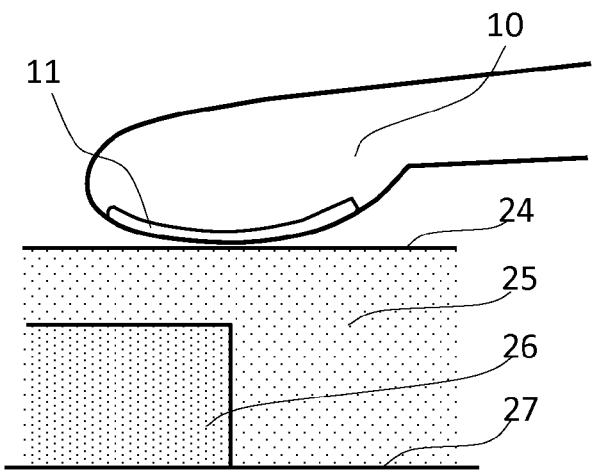
FIGS. 2A through 2C illustrate obtaining stress and strain data resulting from vaginal model tissue deformation and composing a vaginal tactile image.
Figure 2B:
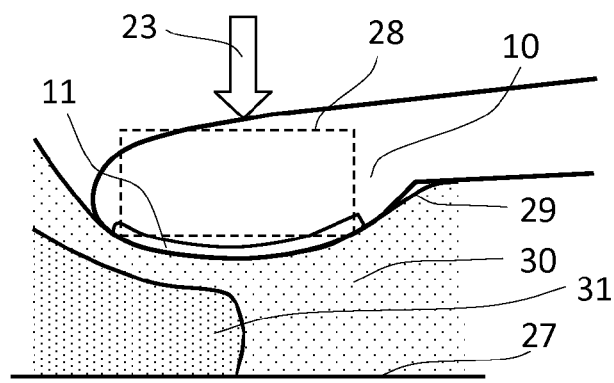
Figure 2C:
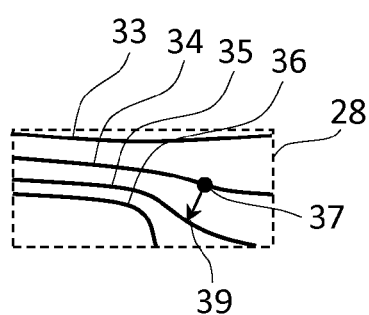

FIG. 2 illustrates obtaining stress and strain data resulting from tissue deformation, composing a vaginal tactile image and calculating a stress gradient. FIG. 2A shows the initial position of the transvaginal probe 10 equipped with a pressure sensor array 11 prior to model tissue deformation. Also shown in FIG. 2B is the transvaginal probe 10 at the point of maximum deformation of the model tissue. FIG. 2C shows a representative tactile image for the deformation of model tissue shown in the lower panel 21.

For simplicity of explanations, the model tissue illustrated in FIG. 2A is composed of a relatively soft tissue part 25 and a relatively hard tissue part 26. The soft part 25 may have a Young's modulus of 3 kPa while the hard part 26 may have a Young's modulus of 10 kPa. The part 25 is covered by a surface layer 24 which is representative of a vaginal wall. The bottom layer of the model tissue rests on a stationary support 27. Panel 21 shows the transvaginal probe 10 deforming the model tissue by applying compression force in the direction of the arrow 23. This results in deformation of the model tissue so that the tissue part 25 is displaced into a deformed tissue part 30 and the tissue part 26 is displaced into a respective deformed tissue part 31. The surface layer 24 is also displaced into a deformed surface layer 29 under applied force from the transvaginal probe 10. The bottom layer of this theoretical model tissue is not deformed or displaced in any way.

During the deformation of the surface layer 24 into the deformed surface layer 29, the position and respective contact stress are recorded for each pressure sensor contacting a corresponding measurement point on the surface layer 24 using the pressure sensor array and the motion tracking sensor. Motion tracking data and pressure sensor data together form a set of stress and strain data for the deforming surface layer 24.

This stress and strain data is then used for composing the vaginal model tissue tactile image 28 shown in FIG. 2B. The three-dimensional vaginal tactile image is defined as a family of constant stress surfaces representing locations of the measurement points when they are under the same level of stress. A two-dimensional vaginal tactile image is a family of curves representing constant tress levels. FIG. 2C shows a cross-section view of the three-dimensional vaginal tactile image in which lines 33-36 represent cross-sections of such surfaces. In the example shown in FIG. 2C, these constant stress surface and corresponding lines 33-36 represent a number of constant stress values increasing for example from 3 kPa to 6 kPa, 8 kPa, and 10 kPa. Other appropriate levels of stress may be selected to be represented as a family of constant stress surfaces.

As discussed above, not all points on each surface represent actual measurement results. In some cases, the exact geometrical location of a particular measurement point when subjected to a selected constant stress is calculated by extrapolating from measured locations of this measurement point and corresponding stress levels assuming a linear model of tissue compression. In fact, a constant stress surface may not have even a single location where the actual measurement took place as most or even all points of the surface may be calculated from the stress and strain data.

Other methods of mathematical processing of the stress and strain data are also envisioned to be within the scope of this invention. For example, the stress and strain data obtained for a plurality of measurement points may be treated as a 3-D cloud of data and each of the constant stress surfaces (which may also be referred to as an iso-surface) may be computed mathematically using the entire set of data.

Elasticity or the capability of substance to be deformed under applied force is defined as the ratio of applied stress to resulting strain. The elasticity image of vagina and surrounding tissue is derived from the stress and strain data collected for a variety of vaginal tissue deformations. The calculation of a ratio of a change in stress value between two near geometrical points of the composed tactile image to a distance between these two points is closely related to the classical definition of elasticity because the distance in the tactile image corresponds to value of resulting strain of a vaginal wall. This ratio is defined as the stress gradient.

Having a recorded set of stress and strain data allows calculating a stress gradient for a single or multiple measurement points within the vaginal tactile image. Taking a point 37 in FIG. 2C for example, a stress gradient is calculated as a ratio of differences in stress values between points 37 and 39 to the distance between the same points 37 and 39. This stress gradient is characterizing the tissue elasticity around the point 37. The calculated stress gradient has two components: a scalar component represented as a number ascribed to each specific point 37 and a vector component at the same location because in a general case the stress gradient value depends on the direction which is characterized by a vector connecting two points. This stress gradient may be calculated in units of kPa/cm.

Elasticity of vaginal tissue is assumed to be linear in the range of applied deformations. In that case, increasing levels of contact pressure will result in generally increasing levels of tissue and probe movement. At the same time, the ratio of stress to strain will remain nearly constant between different levels of applied strain and strain. At least two data points are needed to calculate the ratio of stress to strain. Preferably, such ratio is calculated from a plurality of measurements, such as when recording a curve of stress over strain using the probe to deform the tissue at one location. Additional repeated deformations may allow increasing the accuracy of calculations and avoiding artifacts, for example by detecting the average value of the stress gradient.

The stress gradient may be calculated in a cylindrical coordinate system from vaginal wall surface to deeper tissue, with the longitudinal axis passing through the center of vagina. The stress gradient may also be calculated in an orthogonal coordinate system from vaginal wall surface to deeper tissue in an anterior direction or in a posterior direction.

Figure 3:
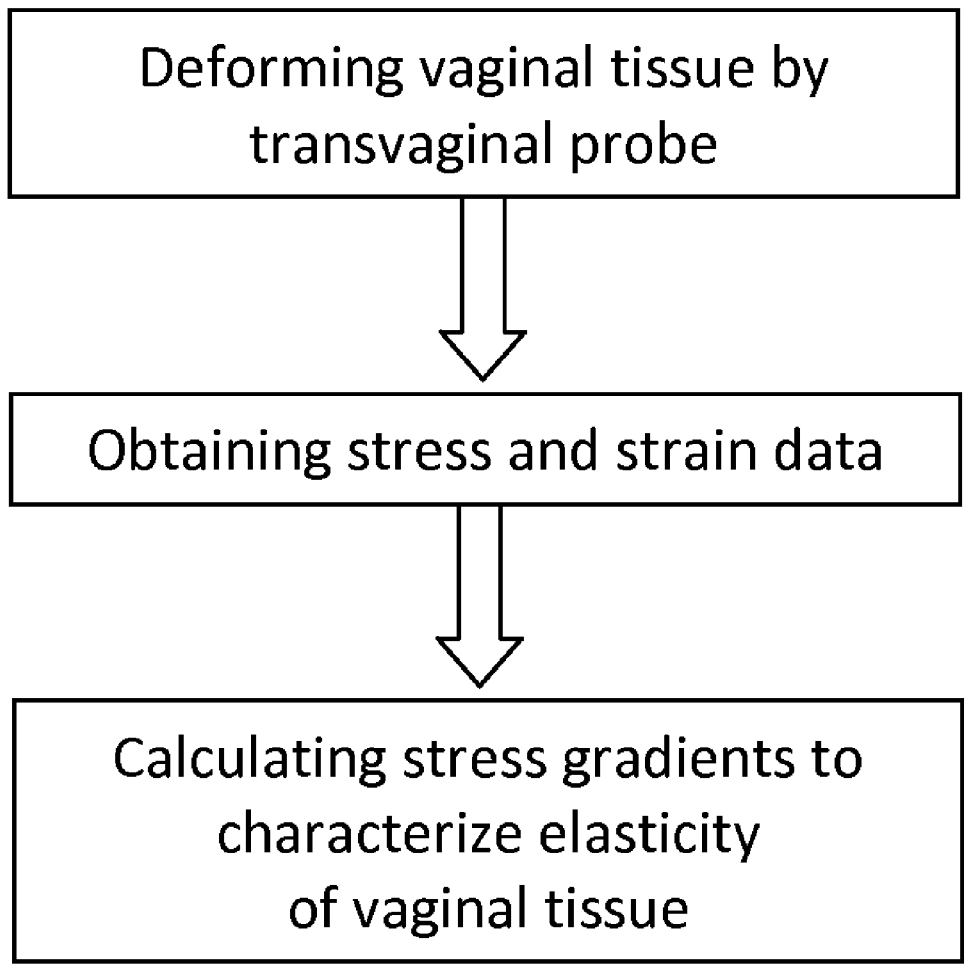
FIG. 3 is a flow chart illustrating one method for characterizing vaginal tissue elasticity.

FIG. 3 is a flow chart illustrating one method for characterizing vaginal tissue elasticity. The method includes deforming the vaginal tissue by a transvaginal probe about at least a first measurement point in step (a); obtaining stress and strain data for the first measurement point using the transvaginal probe in step (b); and calculating a stress gradient from the stress and strain data to characterize elasticity of vaginal tissue in step (c). The method may further include a step of detecting a pelvic organ abnormality condition if the stress gradient is below a predetermined threshold.

Step (a) may include deformation of tissue by compression using a transvaginal probe to press against the tissue a range of pressures from about 1 kPa to about 20 kPa. Alternatively, tissue deformation may be done by a repeated sliding of the transvaginal probe over a predetermined area of vaginal tissue while applying increased levels of pressure thereto. At least two such slidings of the probe over the same predetermined area of the vaginal tissue may be conducted. Importantly, each subsequent pressure may be selected to exceed the previous pressure by at least 1 kPa. All applied pressures may be selected to be within a range from about 1 kPa to about 10 kPa. Step (c) may further include calculating an average stress gradient for a preselected zone of vagina and comparing it against a normal stress gradient for the same preselected zone of vagina. Normal stress gradient may be obtained from clinical data for a plurality of patients, optionally adjusting it for age and other factors.

Figure 4:
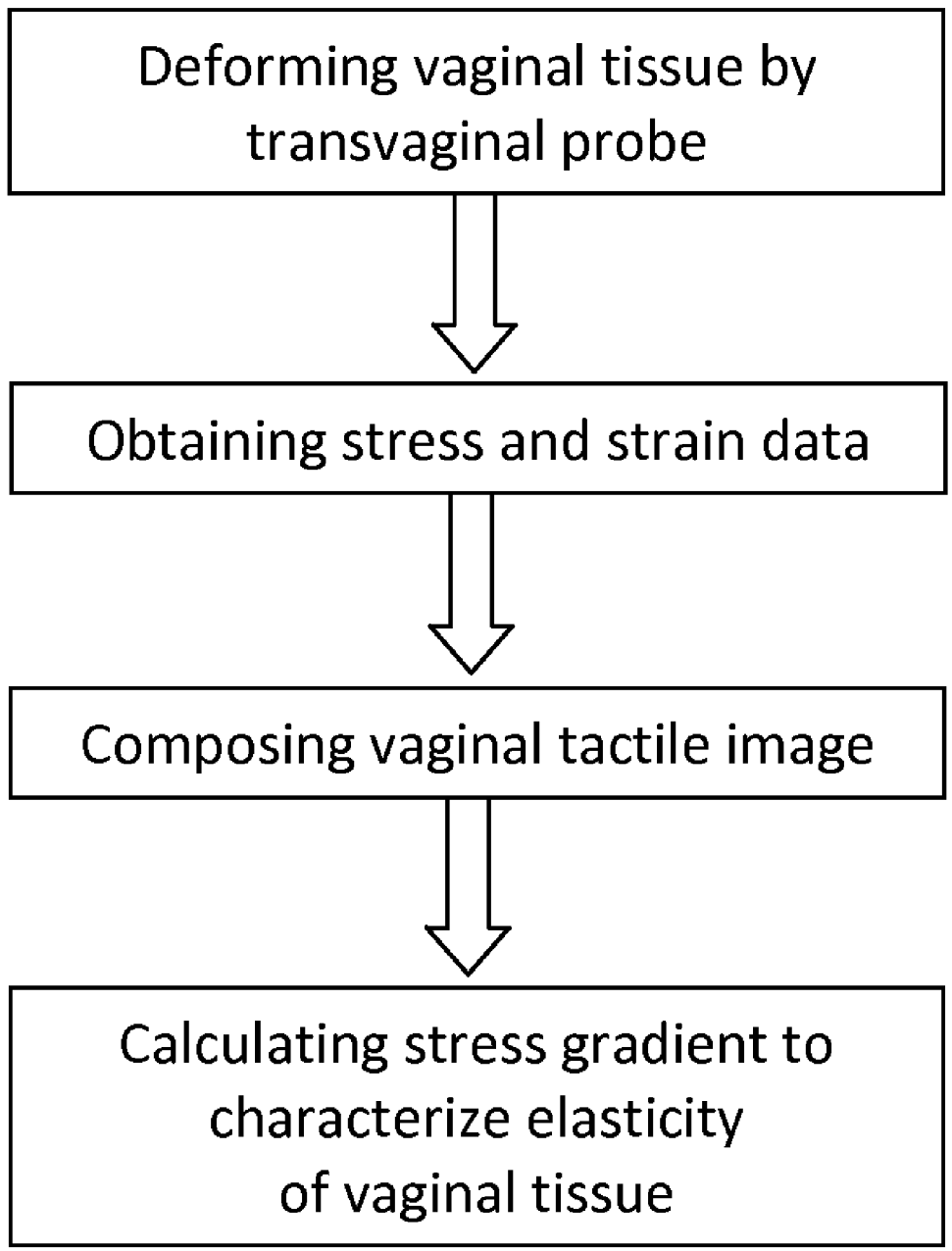
FIG. 4 is a flow chart illustrating another method for characterizing vaginal tissue elasticity and detection of pelvic floor abnormality.

FIG. 4 is a flow chart illustrating another method for characterizing vaginal tissue elasticity. The method generally includes deforming the vaginal tissue by a transvaginal probe about a plurality of measurement points in step (a); obtaining stress and strain data for each measurement point in step (b) resulting from deformation of tissue in step (a); composing a vaginal tactile image in step (c) using the stress and strain data from step (b), in which the vaginal tactile image is a family of constant stress surfaces, each constant stress surface represents locations of measurement points when the vaginal tissue is under a predefined constant level of stress; and calculating a stress gradient for at least one of the points using the vaginal tactile image to characterize elasticity of vaginal tissue in step (d).

Step (a) of tissue deforming may include tissue compression or repeated sliding of a transvaginal probe over at least a preselected area of vagina as generally described above for the method illustrated in FIG. 3.

The plurality of measurement points may be selected to be within an anterior or a posterior wall of vagina. The stress gradient may be calculated as a ratio of stress over strain obtained for the same measurement point. Step (c) may further include a step of detecting a pelvic organ abnormality condition if the stress gradient is below a predetermined threshold. Step (c) may further include calculating an average stress gradient for the plurality of measurement points and comparing it against a normal stress gradient obtained from clinical data for a plurality of patients.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for characterizing elasticity of a vaginal tissue, said method comprising the steps of:
   (a) deforming said vaginal tissue by a transvaginal probe equipped with a pressure sensor array and a motion tracking sensor;
   (b) obtaining stress and strain data for at least two measurement points using said transvaginal probe, said stress and strain data resulting from deformation applied to said vaginal tissue; and
   (c) calculating stress gradients for said two measurement points using said stress and strain data to characterize elasticity of said vaginal tissue.

2. The method as in claim 1 further including a step (d) of detecting a pelvic organ abnormality condition if at least one of said stress gradient is below a predetermined threshold.

3. The method as in claim 1, wherein said stress gradient is a ratio of said stress over said strain.

4. The method as in claim 1, wherein in said deforming in step (a) includes a first sliding of said transvaginal probe over a predetermined area of said vaginal tissue while applying a first pressure thereto, said deforming further includes at least a second sliding of said probe over said same predetermined area of said vaginal tissue while applying a second pressure thereto, said second pressure exceeding said first pressure by at least 1 kPa.

5. The method as in claim 2, wherein said step (c) further includes calculating an average stress gradient for a preselected zone of said vagina, said step (d) further includes comparing said average stress gradient against a normal stress gradient for said same preselected zone of vagina, said normal stress gradient obtained from clinical data for a plurality of patients.

6. A method for characterizing elasticity of a vaginal tissue, said method comprising the steps of:
   (a) deforming said vaginal tissue by a transvaginal probe equipped with a pressure sensor array and a motion tracking sensor about a plurality of measurement points;
   (b) obtaining stress and strain data for each of said measurement points using said pressure sensor array and said motion tracking sensor, said stress and strain data representing said deformation applied to said vaginal tissue by said transvaginal probe;
   (c) composing a vaginal tactile image using said stress and strain data, said vaginal tactile image being a family of constant stress surfaces, each of said constant stress surfaces representing locations of said plurality of measurement points when said measurement points are under a predefined constant stress; and
   (d) calculating a stress gradient for at least one of said measurement points using said vaginal tactile image to characterize elasticity of said vaginal tissue.

7. The method as in claim 6, wherein said deforming in said step (a) includes a first sliding of said transvaginal probe over a predetermined area of said vagina while applying a first pressure thereto, said step (a) further includes at least a second sliding of said transvaginal probe over said same predetermined area of said vagina while applying a second pressure thereto, said second pressure selected to exceed said first pressure by at least 1 kPa.

8. The method as in claim 6, wherein said plurality of measurement points is selected to be located within an anterior wall of vagina.

9. The method as in claim 6, wherein said plurality of measurement points is selected to be located within a posterior wall of vagina.

10. The method as in claim 6, wherein said step (d) further includes calculating said stress gradient as a ratio of said stress over said strain obtained for the same measurement point.

11. The method as in claim 10, wherein said step (c) further includes detecting a pelvic organ abnormality condition if said stress gradient is below a predetermined threshold.

12. The method as in claim 6, wherein said step (c) further includes calculating an average stress gradient for said plurality of measurement points, said step (c) further includes comparing said calculated average stress gradient against a normal stress gradient obtained from clinical data for a plurality of patients.

* * * * *